(12) United States Patent
Dunaway

(10) Patent No.: US 6,696,466 B1
(45) Date of Patent: Feb. 24, 2004

(54) METHODS OF TREATING SELECT NEURONAL INFLAMMATORY DISORDERS USING HYDROXYALKYLQUINOLINES

(76) Inventor: Leslie Joe Dunaway, 2016 Fairway Vista Dr., Louisville, KY (US) 40245

( * ) Notice: Subject to any disclaimer, the term of this patent is extended or adjusted under 35 U.S.C. 154(b) by 0 days.

(21) Appl. No.: 09/657,333

(22) Filed: Sep. 7, 2000

(51) Int. Cl.$^7$ ............................................. A61K 31/47
(52) U.S. Cl. ..................................................... 514/311
(58) Field of Search ................................ 514/311, 312

(56) References Cited

U.S. PATENT DOCUMENTS

| | | | |
|---|---|---|---|
| 4,708,965 A | 11/1987 | Morgan | 514/563 |
| 4,863,958 A | 9/1989 | Belanger et al. | 514/469 |
| 4,912,131 A | 3/1990 | Adams et al. | 514/464 |
| 5,087,638 A | 2/1992 | Belanger et al. | 514/456 |
| 5,266,568 A | 11/1993 | Belley et al. | 514/228.2 |
| 5,270,324 A | 12/1993 | Zamboni et al. | 514/311 |
| 5,428,033 A | 6/1995 | Belley et al. | 514/228.2 |
| 5,492,915 A | 2/1996 | Dereu et al. | 514/311 |
| 5,565,473 A | 10/1996 | Belley et al. | 514/313 |
| 5,709,855 A | 1/1998 | Bockow | 424/93.7 |
| 5,837,690 A | 11/1998 | Rao et al. | 514/26 |
| 5,856,322 A | 1/1999 | Belley et al. | 514/222.2 |
| 5,872,280 A | 2/1999 | Abram et al. | 562/430 |
| 5,952,347 A | 9/1999 | Arison et al. | 514/311 |
| 5,985,937 A | 11/1999 | Bonal de Falgas et al. | 514/737 |

OTHER PUBLICATIONS

Medline Abstract, AN 96379398, 1996, Verdon.*
Verdon, "overuse syndromes of the hand and wrist," Primary Care; Clinics in Office Practice, 1996, vol. 23, No. 2, pp. 305–319.*
Huang et al. "Sports and other soft tissue injuries, tendinitis, bursitis, and occupation–related syndromes," Current Opinion Rheumatology, Mar. 2000, vol. 12, No. 2, pp. 150–154.*
Feuerstein et al. "Clinical Management of carpal tunnel syndrome: a 12 year review of outcomes," American Journal of Industrial Medicine, 1999, vol. 35, pp. 232–245.*
Steinhiber, "5–Lipoxygenase: A target for antiinflammatory Drug revisited," Current Medicinal Chemistry, 1999, vol. 6, pp.71–85.*
"There are Ways to Help prevent Carpal Tunnel"; The Louisville Courier–Journal; Feature Section p.; May 7, 2000; 2 pages.

* cited by examiner

*Primary Examiner*—Shengjun Wang
(74) *Attorney, Agent, or Firm*—Sieberth & Patty, L.L.P.

(57) ABSTRACT

Methods of treating select mammalian disorders using a leukotriene antagonist are described. The methods involve administering to the mammal a therapeutically effective amount of a compound having the formula:

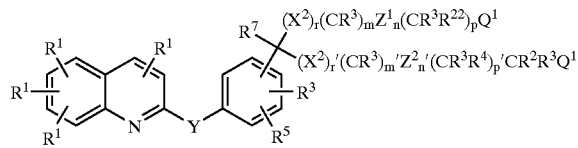

The methods may be employed to treat disorders such as carpal tunnel, cubital tunnel, tarsal tunnel, traumatic spinal cord injury, graying of the scalp hair, thoracic outlet, herpes simplex, herpes zoster, Bell's palsy, multiple sclerosis, and Gillian-Barre.

7 Claims, No Drawings

METHODS OF TREATING SELECT NEURONAL INFLAMMATORY DISORDERS USING HYDROXYALKYLQUINOLINES

TECHNICAL FIELD

This invention relates to methods of treating neuronal inflammatory disorders.

THE INVENTION

Certain hydroxyalkyiquinoline acids and ether acids, as well as their corresponding salts, are known to be leukotriene antagonists. See, e.g., U.S. Pat. Nos. 5,266,568, 5,270,324, 5,428,033, 5,565,473 and 5,856,322. As noted in the foregoing patents, these compounds are known to be useful in the treatment of pulmonary disorders including diseases such as asthma, chronic bronchitis, and related obstructive airway diseases, allergies and allergic reactions such as allergic rhinitis, contact dermatitis, allergic conjunctivitis, and the like, inflammation such as arthritis or inflammatory bowel disease, pain, skin disorders such as psoriasis, a topic eczema, and the like, cardiovascular disorders such as angina, myocardial ischemia, hypertension, platelet aggregation and the like, renal insufficiency arising from ischemia induced by immunological or chemical (cyclosporin) etiology, migraine or cluster headache, ocular conditions such as uveitis, hepatitis resulting from chemical, immunological or infectious stimuli, trauma or shock states such as burn injuries, endotoxemia and the like, allograft rejection, prevention of side effects associated with therapeutic administration of cytokines such as Interleukin II and tumor necrosis factor, chronic lung diseases such as cystic fibrosis, bronchitis and other small and large-airway diseases, cholecystitis; erosive gastritis; erosive esophagitis; diarrhea; cerebral spasm; premature labor; spontaneous abortion; dysmenorrhea; ischemia; noxious agent-induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gastric damage; trauma-or stress-induced cell damage; glycerol-induced renal failure; and cytoprotective activity in gastrointestinal mucosa and prevention of gastric lesions.

However, it has now been found that select hydroxyalquinoline acids (and the pharmaceutically acceptable salts thereof) are useful in the treatment of conditions which are believed to be caused by neuronal inflammation. Neuronal inflammatory disorders share a particular pathophysiology in relation to the select hydroxyalkylquinoline compounds. In particular, compounds which have the biological property in mammals of acting as "leukotriene antagonists" are particularly effective in the treatment of neuronal inflammatory disorders.

Furthermore, it has been discovered that certain hydroxyalkylquinoline acids and their salts can be utilized to treat some disorders which have not been conclusively shown to originate with inflamed neurons. One particularly painful and debilitating group of disorders, members of which have responded remarkably well to treatment with hydroxyalkylquinolines, are those commonly referred to as repetitive motion disorders. In the case of such disorders, hydroxyalkylquinolines not only effectively relieve the symptoms, but often effect a complete cure, allowing return to the same repetitive motion-type activity which caused the disorder without incidence of relapse. Regardless of any previous association with repetitive motion, the disorders referred to hereinafter are considered to be neuronal inflammatory disorders for the purposes of this description, even if it has not been conclusively established that the symptoms of the particular disorder are caused or mediated by inflamed neuronal elements.

Disorders which are known to be neural inflammatory in nature include viral infections, such as Herpes simplexes I and II. The present invention has demonstrated success in the treatment of symptoms of viral infections. Thus a method is provided for the treatment and/or the long term suppression of symptoms of viral infection such as skin lesions and postherpetic neuralgia, as well as other symptoms of viral infection which are neuronal inflammatory in origin.

The present invention has also been successful in halting the course of a condition which has long been suspected by the present inventor to be neuronal inflammatory in origin: the progressive graying of the scalp hair. Thus the present invention provides a method for the treatment and/or long-term suppression of symptoms of scalp hair conditions which are neuronal inflammatory in nature, such as progressive graying.

In addition, the present invention provides a method for treating and/or suppression of symptoms of neuronal inflammatory conditions whose etiology is often partially or fully unknown, some of which are Multiple sclerosis, Guillian-Barre syndrome and Bell's palsy.

Furthermore, the present invention provides a method for the treatment of neuronal inflammatory conditions which originate with external factors, such conditions including traumatic spinal injury.

Moreover, the present invention provides a method for treatment and long term suppression of symptoms associated with disorders previously considered repetitive motion disorders.

The above-described methods comprise administering, to a mammal in need of such treatment, a therapeutically effective amount of a compound having a chemical structural formula as follows:

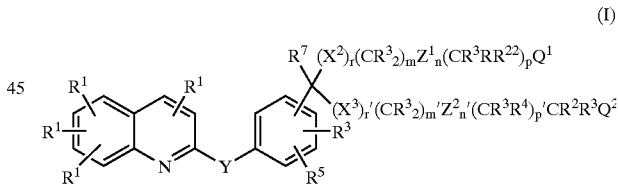

(I)

wherein:

$R^1$ is H, halogen, —$CF_3$, —CN, —$NO_2$, or $N_3$;

$R^2$ is lower alkyl, lower alkenyl, lower alkynyl, —$CF_3$, —$CH_2F$, —$CHF_2$, $CH_2CF_3$, substituted or unsubstituted phenyl, substituted or unsubstituted benzyl, substituted or unsubstituted 2-phenethyl, or two $R^2$ groups joined to the same carbon to form a carbocyclic ring of up to 8 members;

$R^3$ is H or $R^2$;

$R^4$ is halogen, —$NO_2$, —CN, —$OR^3$, —$SR^3$, $NR^3R^3$, $NR^3C(O)R^7$ or $R^3$;

$R^5$ is H, halogen, —$NO_2$, —$N_3$, —CN, —$SR^2$, $NR^3R^3$, —$OR^3$, lower alkyl, or —$C(O)R^3$;

$R^6$ is —$(CH_2)_5$ —$C(R^7R^7)$—$(CH_2)$, —$R^8$ or —$CH_2C(O)NR^{12}R^{12}$;

$R^7$ is H or $C_1$–$C_4$ alkyl;

$R^8$ is the radical W—$R^9$;

$R^9$ contains up to 20 carbon atoms and is (1) an alkyl group or (2) an alkylcarbonyl group of an organic acyclic or monocyclic carboxylic acid;

$R^{11}$ is lower alkyl, —C(O)$R^{14}$, unsubstituted phenyl, or unsubstituted benzyl;

$R^{12}$ is H, or $R^{11}$;

$R^{13}$ is lower alkyl, lower alkenyl, lower alkynyl, —CF$_3$ or substituted or unsubstituted phenyl, benzyl, or 2-phenethyl;

$R^{14}$ is H or $R^{13}$;

$R^{16}$ is H, C$_1$–C$_4$ alkyl, or OH;

$R^{17}$ is lower alkyl, lower alkenyl, lower alkynyl, or substituted or unsubstituted phenyl, benzyl, or 2-phenethyl;

$R^{18}$ is lower alkyl, lower alkenyl, lower alkynyl, —CF$_3$ or substituted or unsubstituted phenyl, benzyl, or 2-phenethyl;

$R^{19}$ is lower alkyl, lower alkenyl, lower alkynyl, —CF$_3$ or substituted or unsubstituted phenyl, benzyl, or 2-phenethyl;

$R^{21}$ is H or $R^{17}$;

$R^{22}$ is $R^4$, CHR$^7$OR$^3$, or CHR$^7$ SR$^2$;

m is 0–8;

m' is 2 or 3;

n and n' are independently 0 or 1, p and p' are independently 0–8;

m+n+p is 1–10 when r is 1 and $X^2$ is O, S, S(O), or S(O)$_2$;

m+n+p is 0–10 when r is 1 and $X^2$ is CR$^3$R$^{16}$;

m+n+p is 0–10 when r is 0;

m'+n'+p' is 2–10;

r and r' are independently 0 or 1;

s is 0–3;

$Q^1$ is —C(O)OR$^3$, 1H (or 2H)-tetfazol-5-yl, —C(O)OR$^6$, —C(O)NHS(O)$_2$R$^{13}$, —CN, —C(O)NR$^{12}$R$^{12}$, NR$^{21}$S(O)$_2$R$^{13}$, —NR$^{12}$C(O)NR$^{12}$R$^{12}$, —NR$^{21}$C(O)R$^{18}$, —OC(O)NR$^{12}$R$^{12}$, —C(O)R$^{19}$, —S(O)R$^{18}$, —S(O)$_2$R$^{18}$, —S(O)$_2$ NR$^{12}$R$^{12}$, —NO$_2$, —NR$^{21}$C(O)OR$^{17}$, —C(NR$^{12}$R$^{12}$)=NR$^{12}$, —C(R$^{13}$)=NOH;

$Q^2$ is OH;

W is O, S, or NR$^3$;

$X^2$ and $X^3$ are independently O, S, S(O), S(O)$_2$, or CR$^3$R$^{16}$; with the proviso that at least on is S or SO$_2$;

Y is —CR$^3$=CR$^3$—

$Z^1$ and $Z^2$ are independently —HET(—R$^3$—R$^5$)—;

HET is the diradical of a benzene, a pyridine, a furan, or a thiophene;

or a pharmaceutically acceptable salt thereof. The term "pharmaceutically acceptable salt" refers to a salt that retains the desired biological activity of the parent compound and does not impart any undesired toxicological effects, e.g., an acid or base addition salt.

Preferred is a compound having a chemical structural formula as follows:

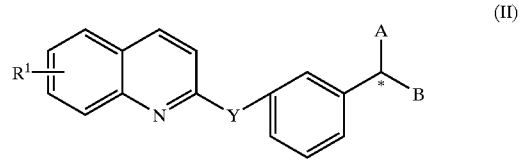

(II)

wherein the substituents are as follows:

| * | $R^1$ | Y | A | B |
|---|---|---|---|---|
| RS | 7-Cl | CH=CH | SCH$_2$CHMeCO$_2$H | (1,3-phe)CMe$_2$OH |
| RS | 7-Cl | CH=CH | SCH$_2$CHMeCO$_2$H | (1,4-phe)CMe$_2$ OH |
| RS | 7-Cl | CH=CH | SCH$_2$CHEtCO$_2$ H | (1,3-phe)CMe$_2$ OH |
| RS | 7-Cl | CH=CH | SCH$_2$CHEtCO$_2$ H | (1,2-phe)CMe$_2$ OH |
| RS | 7-Cl | C≡C | SCH$_2$CHMeCO$_2$ H | (CH$_2$)$_2$ (1,2-phe)CMe$_2$ OH |
| S | 7-Cl | C≡C | SCH$_2$(S)CHMeCO$_2$H | (CH$_2$)$_2$ (1,2-phe)CMe$_2$ OH |
| RS | 7-Cl | C≡C | SCH$_2$CHEtCO$_2$ H | (CH$_2$)$_2$ (1,2-phe)CMe$_2$ OH |
| RS | 7-Cl | C≡C | S(CH$_2$)$_2$CO$_2$ H | (CH$_2$)$_2$ (1,2-phe)CMe$_2$ OH |
| RS | 7-Cl | CH=CH | SCH$_2$CHMeCO$_2$ H | (CH$_2$)$_2$ (1,2-phe)CMe$_2$ NH$_2$ |
| RS | 7-Cl | CH=CH | SCH$_2$CHEtCO$_2$ H | (CH$_2$)$_2$ (1,2-phe)CMe$_2$ NHMe |
| RS | 7-Cl | CH=CH | SCH$_2$CHEtCO$_2$ H | (CH$_2$)$_2$ (1,2-phe)CMe$_2$ NMe$_2$ |
| RS | 7-Br | C≡C | SCH$_2$CHEtCO$_2$ H | (CH$_2$)$_2$ (1,2-phe)CMe$_2$ OH |
| S | 7-Cl | CH=CH | SCH$_2$CH(CH$_2$CH=CH$_2$)CO$_2$H | (CH$_2$)$_2$ (1,2-phe)CMe$_2$ OH |
| S | 7-Cl | CH=CH | SCH$_2$CHEtCO$_2$H | (CH$_2$)$_2$(1,2-phe)C(CH$_2$OCH$_2$)OH |

Particularly preferred as the compound is 1-(((1(R)-(3-(2-(7-chloro-2-quinolinyl)ethenyl)phenyl)-3-(2-(2-hydroxy-2-propyl)phenyl)propyl)thio)methyl)cyclopropaneacetic acid or a pharmaceutically acceptable salt thereof, and in particular the monosodium salt thereof (i.e., montelukast sodium), which is the active ingredient in the pharmaceutical marketed by Merck & Co., Inc. under the trademark, Singulair®. This and related compounds, including methods of producing such compounds, are described in greater detail in U.S. Pat. No. 5,565,473, the disclosure of which is incorporated herein by reference.

This invention also provides an article of manufacture for human pharmaceutical use, comprising packaging material and a container comprising 1-(((1(R)-(3-(2-(7-chloro-2-quinolinyl)ethenyl)phenyl)-3-(2-(2-hydroxy-2-propyl) phenyl)propyl)thio)methyl)cyclopropaneacetic acid or a pharmaceutically acceptable salt thereof, wherein said packaging material comprises a label which indicates that said cyclopropaneacetic acid, or said pharmaceutically acceptable salt thereof, is suitable for treatment, or alleviation of symptoms, often or more disorders selected from the group consisting of carpal tunnel, cubital tunnel, tarsal tunnel, traumatic spinal cord injury, graying of scalp hair, thoracic outlet, herpes simplex, herpes zoster, Bell's palsy, multiple sclerosis, and Gillian-Barre.

These and other embodiments and features of the invention will become still further apparent from the ensuing description, examples and appended claims.

DETAILED DESCRIPTION OF THE INVENTION

When utilizing hydroxyalkyl quinolines to treat the aforementioned conditions, the compound can be introduced into the body by oral administration, (i.e., by ingestion of a tablet, pill, liquid suspension or the like), by sub-dermal injection, or other means. If taken orally, it is preferable to use a dose of about 4 to about 10 milligrams per day. If administered by injection, it is preferable to utilize a dose of about 1 to about 10 milligrams per injection, about 2–4 times per monthly. The entire daily dosage can be taken as a single dose, or it can be administered as two or more smaller doses taken at appropriate intervals. However, preferred dosages, preferred modes of administration, and subdivision of dosages vary somewhat with the condition or disease for which treatment is sought. Suggestions pertaining to particular conditions are given below.

Hydroxyalkylquinoline compounds can be used for the relief of symptoms due to active viral infections. In particular, the active ingredient of Singulair® can relieve blisters and skin lesions such as 1) skin lesions on the face, lip and oral mucosa overlying soft tissue due to an active Herpes Simplex I infection (HSV-I); 2) skin lesions on the genitals and anus due to an active Herpes Simplex I (HSV-I) infection or Herpes Simplex II infection (HSV-II); and 3) variously located skin lesions due to an active infection of Herpes zoster (chicken pox virus). The standard oral dose of about 4 to about 10 milligrams is appropriate for the treatment of existing blisters in a patient.

Hydroxyalkylquinolines can be administered at any time during the presence of the blisters. However, best results are obtained when treatment is initiated as soon as the initial symptoms of blistering are detected.

It is preferable that the patient continue to take an effective amount of a composition of this invention until blisters and pain have subsided. Treatment time can be expected to be in the range of from about 5 to about 10 days. In most cases, patient experiences complete relief in a time in the range of from about 2 to about 4 days.

Hydroxyalkylquinolines can also be used to treat or prevent or reduce the severity of the localized pain caused by viral infection, typically following the resolution of skin blisters. In particular, such compounds are effective in treating post-herpetic neuralgia such as is often associated with chicken pox virus infection. The dosages and means of administration are as noted in the first paragraph of the "Detailed Description." It is preferred that the dosages be administered orally for a period of two to four weeks. Treatment can be initiated at any time after the appearance of blisters, from the first appearance to crusting and resolution. However, the likelihood of complete prevention of neuralgia, as opposed to merely reducing its severity, is increased with promptness of treatment. It is preferred that the patient continue treatment for the duration of the pain. In severe cases, it may be advisable to administer continuous treatment. Most patients can be expected to begin experiencing relief within from about 10 to about 21 days.

Other symptoms of the aforementioned viral infections which respond to the administration of hydroxyalkylquinoline compounds are the localized itching, burning or tingling, often for prolonged periods, which accompany the infection and generally closely precede the development of blisters. The dosages and means of administration are as given in the first paragraph of the "Detailed Description."

Furthermore, if hydroxyalkylquinoline compounds are administered after the onset of localized irritation (i.e., itching, burning or tingling), but before the onset of blistering, it can be used to prevent blisters or reduce their severity. In order to prevent blistering, it is preferable to begin treatment within about forty eight hours of the onset of the localized irritation, however, in some cases, even at later times, the administration of hydroxyalkylquinoline compounds can prevent the formation of blisters. The dosages and means of administration are as given in the first paragraph of the "Detailed Description." It is advisable to treat patient with hydroxy alkyl quinoline compounds until the localized irritation subsides, or, if sores develop, until the sores resolve.

Moreover, the administration of appropriate dosages of hydroxyalkylquinoline compounds can be utilized for the long term management of dormant viral infections. For example, hydroxyalkylquinoline compounds can effectively suppress the periodic appearance of stress-induced sores (often induced by overwork, too little sleep, etc.) in a patient with a latent HSV-I or HSV-II infection. A patient can be treated on a continual basis. The dosages and means of administration are as given in the first paragraph of the "Detailed Description."

However, long term suppression of virally-induced pain and blistering can be accomplished by treating the patient on a schedule of intervals which anticipate 1) a sore forming cycle manifested by a particular patient, or 2) stresses to which a patient is, will be, or is likely to be exposed. Examples of such stresses are trauma to self, a friend or a family member; occupational stresses; and the like.

In the inhibition of scalp hair graying, it is advisable to begin treatment before all the scalp hair has grayed. Preferably, only small patches of gray are present. Treatment is on a continuous basis, and interruptions in treatment can result in the resumption of graying. The dosages and means of administration are as given in the first paragraph of the "Detailed Description."

Disorders such as Bell's Palsy, Gillian-Barre Syndrome and Multiple Sclerosis, the etiology of which is unknown and which are thought be the result of virus-initiated neural inflammation, are likely candidates for treatment with hydroxyalkyl quinoline compounds. The dosages and means of administration are as given in the first paragraph of the "Detailed Description." It is preferable to treat Bell's Palsy and Gillian-Barre Syndrome with oral dosages immediately after the onset of symptoms. In the case of Bell's Palsy, such symptoms include facial numbness, weakness or lack of motor control in the facial muscles and lack of taste in the anterior portion of the tongue. A symptom of Guillian-Barre Syndrome which can be expected to improve with the administration of hydroxyalkylquinoline compounds is the accompanying extensive muscular weakness.

In the case of Multiple Sclerosis, treatment with hydroxyalkylquinolines can be expected to reduce the severity of symptoms and number of relapses, the symptoms including, e.g., numbness, weakness and neurogenic pain. A preferred manner of treatment is intrathecal injection of hydroxyalkyl quinoline compounds at the time of diagnosis, with additional injections as long as patient manifests symptoms. Those hydroxyalkylquinoline compounds which have the capacity to penetrate the blood-brain barrier can be administered orally. With such compounds, it is most preferable that oral administration accompany periodic intrathecal injection. Such oral administration can be performed daily, with injections as frequent as two to four times per month.

Traumatic spinal cord injury can be expected to respond to treatment with hydroxyalkyl quinoline compounds. The dosages and means of administration are as described above in the first paragraph of the "Detailed Description." However, it is preferred to begin treatment immediately following the occurrence of spinal cord injury. Such treatment preferably consists of daily oral administration given in conjunction with high doses of intravenous and/or oral steroids. Such treatment preferably continues until such a time as the inflammatory neuronal response to the injury is maximally diminished or eliminated.

Hydroxyalkyl quinoline compounds can also be expected to be useful in treating disorders, heretofore thought to have been caused by swelling of soft tissue and known as repetitive motion disorders, but which may be due instead to neuronal inflammation. In the treatment of carpal tunnel, cubital tunnel, tarsal tunnel and thoracic outlet syndromes, the dosages and means of administration are as given above in the first paragraph of the "Detailed Description." A preferred treatment is the oral administration of hydroxyalkylquinoline compounds for four to eight weeks and/or intermittently as symptoms occur. Another preferred treatment is the injection of the standard injectable dose of the presently described leukotriene antagonists at or near the site of neuronal compression. Such injections may be performed intermittently, or only once. The intended dose can be delivered as a single injection, or as a series of injections, each containing an amount of the hydroxyalkylquinoline which is less than the intended dose.

The pharmaceutical compositions of this invention may be packaged in a variety of ways depending upon the method used for administering the drug. Generally, an article for distribution includes packaging material and a container which contains the pharmaceutical formulation in an appropriate form. Suitable containers are well-known to those skilled in the art and include materials such as bottles (plastic and glass), sachets, ampoules, plastic bags, metal cylinders, blister packs, silica gel desiccant canisters and the like. The container may also include a tamper-proof assemblage to prevent indiscreet access to the contents of the package. In addition to the container, the article further comprises packaging material comprised of a label deposited upon or packaged with the container, the label describing the contents of the container and indicating that contents of the container is suitable for treatment, or alleviation of symptoms, of one or more disorders selected from the group consisting of carpal tunnel, cubital tunnel, tarsal tunnel, traumatic spinal cord injury, graying of scalp hair, thoracic outlet, herpes simplex, herpes zoster, Bell's palsy, multiple sclerosis, and Gillian-Barre. The label may also include appropriate warnings.

Examples 1–7 demonstrate the effectiveness of a preferred hydroxyalkylquinoline acid (or the pharmaceutically acceptable salt thereof) in treating and/or suppressing the symptoms of repetitive trauma disorders such as carpal tunnel, cubital tunnel, and thoracic outlet syndromes.

EXAMPLE 1

A carpenter who was experiencing the symptoms of carpal tunnel syndrome was treated with 10 mg of Singulair® per day, taken orally, for four weeks. He continued to perform his daily occupational activities throughout the period of treatment. He obtained complete remission of symptoms. Following cessation of treatment, the symptoms recurred. Patient was then treated for short courses of 10 mg of Singulair® per day, whenever symptoms were present, until symptoms subsided.

EXAMPLE 2

A patient who worked as a billing clerk had carpal tunnel symptoms which had not responded to non-surgical methods of treatment. Patient was treated with Singulair® at 10 mg daily, taken orally. After six weeks, she experienced complete resolution of her carpal tunnel symptoms. Though she continued her occupational activities as a billing clerk, after forty weeks, she remained symptom-free.

EXAMPLE 3

A patient who works as a data entry clerk, experienced severe carpal tunnel symptoms. She ceased her occupational activities and began treatment with Singulair® at 10 mg per day, taken orally. After four weeks of therapy, her symptoms had completely resolved, and she returned to work, continuing the Singulair® treatment. Upon recheck in two weeks, she remained symptom-free. At this time, treatment with Singulair® was discontinued, and patient remained symptom-free thereafter.

EXAMPLE 4

Patient was an insurance clerk who experienced severe carpal tunnel symptoms which had not abated, even after carpal tunnel decompression surgery. For years following surgery, she had experienced severe carpal tunnel symptoms. After six weeks of therapy with Singulair® at 10 mg per day taken orally, she experienced complete resolution of her symptoms, despite the fact that she continued routine occupational activities. When treatment was stopped, her symptoms rapidly returned. Symptoms abated with resumption of treatment, and with continuing treatment, she remains symptom-free.

EXAMPLE 5

Patient was an assembly line worker at an automobile production facility who was experiencing symptoms of carpal tunnel syndrome was treated with 10 mg of Singulair® per day taken orally. He continued to perform his daily occupational activities and noted that his symptoms abated after six weeks of treatment. He required continuous treatment with 10 mg of Singulair® per day taken orally to maintain remission of his symptoms.

EXAMPLE 6

Patient was a golfer who experienced symptoms of cubital tunnel syndrome. Lengthy treatments with multiple non-steroidal anti-inflammatory drugs, cessation of the causative activity (golf), and use of elbow splints failed to relieve patient's symptoms. Patient was treated with Singulair® at 10 mg daily, taken orally. Symptoms were entirely abated after four weeks. No further treatment was required despite his return to his regular golfing activity.

EXAMPLE 7

Patient exhibited symptoms of thoracic outlet syndrome including a pain radiating down the left arm, a burning sensation beneath the left scapula, weakness of the left hand, and intermittent numbness of the left hand. Patient was treated with Singulair® at 10 mg per day taken orally. After four weeks, symptoms had completely resolved. No further treatment was required.

Examples 8–12 demonstrate the effectiveness of a preferred hydroxyalkylquinoline acid (or the salt thereof) in the treatment of Herpes simplex I and II (HSV I and II), a latent latent viral disease.

EXAMPLE 8

Patient had recently discontinued use of Singulair® as a treatment for asthma. Five days later, patient developed a cold sore, possibly caused by excessive exposure to ultraviolet light. The cold sore resolved in three days after treatment with Singulair® was resumed. The rate of resolution was faster than the resolution of previous sores which were treated with antiviral treatments such as those marketed under the trademarks Zovirax® or Famvir® (approximately seven to ten days). During the subsequent two years, patient took Singulair® on a daily basis (10 mg, twice a day). In that time period, patient was exposed to levels of ultraviolet light which were as high as those which had possibly induced the sore, yet no new sore developed.

EXAMPLE 9

A patient who had a history of developing an average of two cold sores per month was treated with Singulair® at 10 mg per day, taken orally. No cold sore was present at the time therapy was started. Patient remained free of cold sores with continuous daily treatment for ten months. Within five days of termination of treatment, a cold sore developed. The patient restarted treatment, and remained free of cold sores as of thirteen months after resumption of treatment.

EXAMPLE 10

Patient had post-herpetic neuralgia due to a latent Herpes infection. Neuralgia developed despite initial treatment with anti-viral agents as per standard treatment recommendations. Patient began treatment with Singulair® (10 mg per day, taken orally). The post-herpetic neuralgia resolved in ten days. No further treatment was required.

EXAMPLE 11

Patient had postherpetic neuralgia due to a latent Herpes infection. Neuralgia developed despite initial treatment with anti-viral agents as per standard treatment recommendations. Patient began treatment with Singulair® (10 mg per day, taken orally). The post-herpetic neuralgia resolved in 14 days. No further treatment was required.

Example 12 demonstrates the effectiveness of a preferred hydroxyalkylquinoline acid (or the salt thereof) in inhibiting the natural graying process of scalp hair.

EXAMPLE 12

Patient had noted the onset of graying of the temple regions of his hair. No progression of the graying process in the temple region or development of graying in any other scalp areas noted after two years and four months of continuous treatment with Singulair® (10 mg per day, taken orally).

The disclosure of each patent and patent application referenced above is incorporated herein by reference to the fullest extent and for all purposes as may be permitted by law.

This invention is susceptible to considerable variation in its practice. Therefore, the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A method for the effective treatment and suppression of symptoms of carpal tunnel syndrome in a mammal, such a method being comprised of administering to a mammal in need of such treatment a therapeutically effective amount of montelukast, or a pharmaceutically acceptable salt thereof, in a therapeutically effective period, wherein the suppressed symptoms include pain.

2. A method according to claim 1 wherein the mammal is man.

3. A method according to claim 2 wherein the administering of the montelukast, or a pharmaceutically acceptable salt thereof, into the body of the mammal is by oral administration or by sub-dermal injection.

4. A method according to claim 3 wherein the therapeutically effective amount of montelukast, or a pharmaceutically acceptable salt thereof, when administered by oral administration is in the range of about 4 to about 10 milligrams per day.

5. A method according to claim 3 wherein the therapeutically effective amount of montelukast, or a pharmaceutically acceptable salt thereof, when administered by sub-dermal injection is in the range of about 1 to about 10 milligrams per injection, and the injection is administered in the range of about 2 to about 4 times per month.

6. A method according to claim 4 wherein the therapeutically effective period is in the range of about 4 to about 8 weeks.

7. A method according to claim 5 wherein the site of sub-dermal injection is at or near a site of neuronal compression.

* * * * *